United States Patent
Lifshitz-Liron et al.

(10) Patent No.: US 7,250,533 B2
(45) Date of Patent: Jul. 31, 2007

(54) PROCESS FOR PREPARING CINACALCET HYDROCHLORIDE

(75) Inventors: Revital Lifshitz-Liron, Hertzlia (IL); Amihai Eisenstadt, Ramat-Hasharon (IL); Shlomit Wizel, Petah Tiqva (IL); Sharon Avhar-Maydan, Givataym (IL); Yuriy Raizi, Natanya (IL); Revital Ramaty, Ramat-Hasharon (IL)

(73) Assignee: Teva Pharmaceutical Industries Ltd, Petah Tiqva (IL)

(*) Notice: Subject to any disclaimer, the term of this patent is extended or adjusted under 35 U.S.C. 154(b) by 0 days.

(21) Appl. No.: 11/435,430

(22) Filed: May 16, 2006

(65) Prior Publication Data

US 2007/0043243 A1 Feb. 22, 2007

Related U.S. Application Data

(60) Provisional application No. 60/681,671, filed on May 16, 2005, provisional application No. 60/684,152, filed on May 23, 2005, provisional application No. 60/698,613, filed on Jul. 11, 2005, provisional application No. 60/702,918, filed on Jul. 26, 2005, provisional application No. 60/734,669, filed on Nov. 7, 2005, provisional application No. 60/738,827, filed on Nov. 21, 2005, provisional application No. 60/750,910, filed on Dec. 15, 2005, provisional application No. 60/696,981, filed on Jul. 5, 2005, provisional application No. 60/697,111, filed on Jul. 6, 2005, provisional application No. 60/701,232, filed on Jul. 20, 2005, provisional application No. 60/706,910, filed on Aug. 9, 2005, provisional application No. 60/735,126, filed on Nov. 8, 2005, provisional application No. 60/794,804, filed on Apr. 24, 2006, provisional application No. 60/739,215, filed on Nov. 22, 2005, provisional application No. 60/742,626, filed on Dec. 5, 2005, provisional application No. 60/730,050, filed on Oct. 24, 2005, provisional application No. 60/732,083, filed on Oct. 31, 2005, provisional application No. 60/733,008, filed on Nov. 2, 2005, provisional application No. 60/741,787, filed on Dec. 1, 2005.

(51) Int. Cl.
C07C 211/00 (2006.01)

(52) U.S. Cl. .................................................. 564/336
(58) Field of Classification Search .................. None
See application file for complete search history.

(56) References Cited

U.S. PATENT DOCUMENTS

| | | | |
|---|---|---|---|
| 4,966,988 | A | 10/1990 | Schinski et al. |
| 5,648,541 | A | 7/1997 | Van Wagenen et al. |
| 6,011,068 | A | 1/2000 | Nemeth et al. |
| 6,031,003 | A | 2/2000 | Nemeth et al. |
| 6,211,244 | B1 | 4/2001 | Van Wagenen et al. |
| 6,313,146 | B1 | 11/2001 | Van Wagenen et al. |
| 2005/0147669 | A1 | 7/2005 | Lawrence et al. |
| 2005/0234261 | A1 | 10/2005 | Wilken et al. |

OTHER PUBLICATIONS

"Sensipar (Cinacalcet HCl) Tablets" Summary Basis of Approval of New Drug Application #21-688 By FDA, (2004).
J. Iqbal, et al. "Cinacalcet Hydrochloride" *IDrugs*, vol. 6, No. 6, p. 587-592, (2003).
L.A. Sorbera, et al. "Cinacalcet Hydrochloride" *Drugs of the Future*, vol. 27, No. 9, p. 831-836, (2002).
X. Wang, et al. "Synthesis of Cinacalcet Congeners" *Tetrahedron Letters*, vol. 45, p. 8355-8358, (2004).
Synder, L.R. et al., *Introduction To Modern Liquid Chromatography*, 2nd Ed., (1979), pp. 549-572, John Wiley & Sons, Inc.
Strobel, H.A. et al., *Chemical Instrumentation: A Systematic Approach*, 3rd Ed., (1989), pp. 391-393, 879-894, 922-925, 953.
Battistuzzi et al. "An Efficient Palladium-Catalyzed Synthesis of Cinnamaldehydes from Acrolein Diethyl Acetal and Aryl Iodides and Bromides" *Organic Letters*, vol. 5, No. 5, p. 777-780, (2003).
Berthiol et al. "Direct Synthesis Of Cinnamaldehyde Derivatives By Reaction Of Aryl Bromides With 3,3-Diacetoxypropene Catalyzed By A Palladium-Tetraphosphine Complex" *Catalysis Letters* vol. 102, Nos. 3-4, pp. 281-284, (2005).
Soai et al. "Sodium Borohydride-t-Butyl Alcohol-Methanol As An Efficient System for the Selective Reduction of Esters" *Synthetic Communication*, vol. 12 (6), pp. 463-467, (1982).
Streitwleser, *Introduction to Organic Chemistry*, Ch 15, pp. 376-403, (1976).
Battistuzzi et al. "3-Arylpropanoate Esters Through The Palladium-Catalyzed Reaction of Aryl Halides with Acrolein Diethyl Acetal" Synlett, No. 8, pp. 1133-1136, (2003).

*Primary Examiner*—Thurman K. Page
*Assistant Examiner*—Kellette Gale
(74) *Attorney, Agent, or Firm*—Kenyon & Kenyon LLP

(57) ABSTRACT

Processes for preparing cinacalcet are provided.

45 Claims, No Drawings

PROCESS FOR PREPARING CINACALCET HYDROCHLORIDE

RELATED APPLICATIONS

This application claims the benefit of U.S. provisional application Nos. 60/681,671, filed May 16, 2005; 60/684,152, filed May 23, 2005; 60/698,613, filed Jul. 11, 2005; 60/702,918, filed Jul. 26, 2005; 60/734,669, filed Nov. 7, 2005; 60/738,827, filed Nov. 21, 2005; 60/750,910, filed Dec. 15, 2005; 60/696,981, filed Jul. 5, 2005; 60/697,111, filed Jul. 6, 2005; 60/701,232, filed Jul. 20, 2005; 60/706,910, filed Aug. 9, 2005; 60/735,126, filed Nov. 8, 2005; 60/794,804, filed Apr. 24, 2006; 60/739,215, filed Nov. 22, 2005; 60/742,626, filed Dec. 5, 2005; 60/730,050, filed Oct. 24, 2005; 60/732,083, filed Oct. 31, 2005; 60/733,008, filed Nov. 2, 2005; and 60/741,787, filed Dec. 1, 2005, hereby incorporated by reference in their entirety.

FIELD OF INVENTION

The invention is directed to a process for preparing Cinacalcet, (R)-α-methyl-N-[3-[3-(trifluoromethyl)phenyl]propyl]-1-naphthalenemethane amine.

BACKGROUND OF THE INVENTION (R)-α-methyl-N-[3-[3-(trifluoromethyl)phenyl]propyl]-1-naphthalenemethane amine (herein "Cinacalcet" or "CNC") has a CAS number of 226256-56-0, a formula of $C_{22}H_{22}F_3N$ and the following structure:

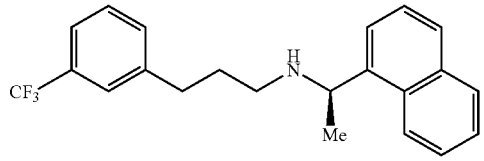

This molecule is the free base form of Cinacalcet hydrochloride (herein "CNC-HCl"), having a CAS number of 364782-34-3 and the following structure:

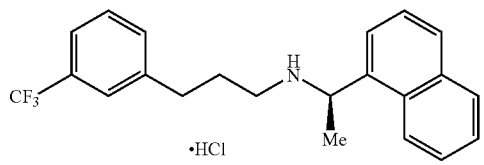

CNC-HCl is marketed as SENSIPAR™, and is the first drug in a class of compounds known as calcimimetics to be approved by the FDA.

Calcimimetics are a class of orally active, small molecules that decrease the secretion of PTH by activating calcium receptors. The secretion of PTH is normally regulated by the calcium-sensing receptor. Calcimimetic agents increase the sensitivity of this receptor to calcium, which inhibits the release of parathyroid hormone, and lowers parathyroid hormone levels within a few hours. Calcimimetics are used to treat hyperparathyroidism, a condition characterized by the over-secretion of PTH that results when calcium receptors on parathyroid glands fail to respond properly to calcium in the bloodstream. Elevated levels of parathyroid hormone (PTH), an indicator of secondary hyperparathyroidism, are associated with altered metabolism of calcium and phosphorus, bone pain, fractures, and an increased risk for cardiovascular death. As a calcimimetic, CNC-HCl is approved for treatment of secondary hyperparathyroidism in patients with chronic kidney disease on dialysis. Treatment with CNC-HCl lowers serum levels of PTH as well as the calcium/phosphorus ion product, a measure of the amount of calcium and phosphorus in the blood.

U.S. Pat. No. 6,011,068 discloses inorganic ion receptor activity, especially calcium receptor-active molecules, such as those having the general structure of Cinacalcet.

U.S. Pat. No. 6,211,244 discloses calcium receptor-active compounds related to Cinacalcet and methods of making such compounds. In accordance with the patent, Cinacalcet may be produced by reacting 1-acetyl naphthalene with 3-[3-(trifluoromethyl)phenyl]propylamine in the presence of titanium isopropoxide to produce an imine corresponding to Cinacalcet, followed by treatment with methanolic sodium cyanoborohydride and resolution of the racemic Cinacalcet base by chiral liquid chromatography, according to Scheme 1:

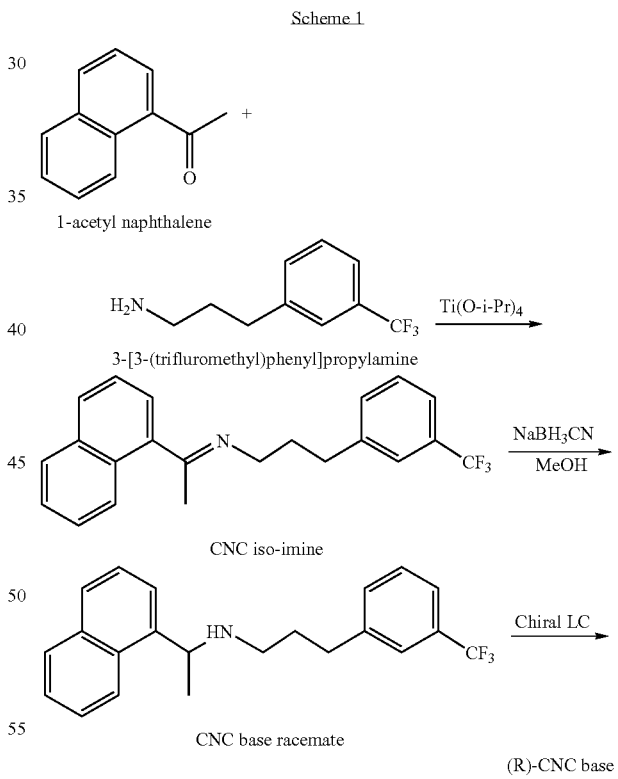

Similarly, using the process disclosed in U.S. Pat. No. 6,211,244, as well as DRUGS OF THE FUTURE (2002) 27 (9): 831 the desired Cinacalcet enantiomer may be produced by reacting (R)-1-(1-naphthyl)ethylamine with 3-[3-(trifluoromethyl)phenyl]propionaldehyde in the presence of titanium isopropoxide to produce the imine that corresponds to Cinacalcet, followed by treatment with ethanolic sodium cyanoborohydride, according to the following scheme:

Scheme 2

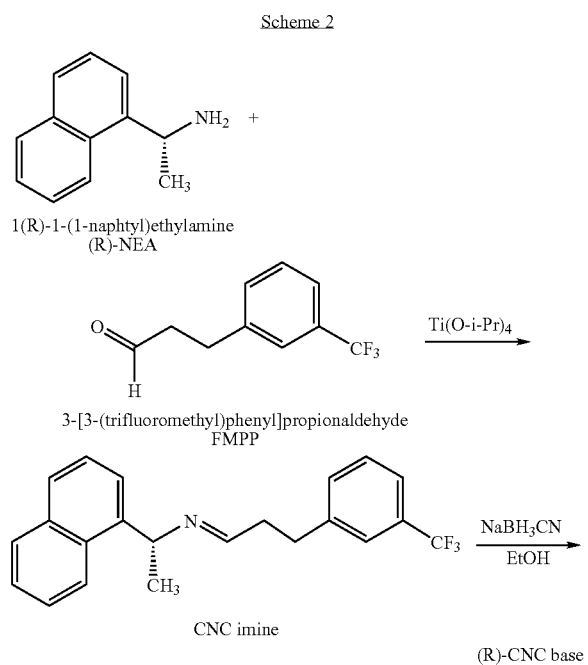

1(R)-1-(1-naphtyl)ethylamine
(R)-NEA

3-[3-(trifluoromethyl)phenyl]propionaldehyde
FMPP

CNC imine (R)-CNC base

U.S. Pat. No. 6,211,244 discloses an additional process for the synthesis of Cinacalcet. This process involves treating 3-trifluoromethylcinnamonitrile, which can be prepared as disclosed in U.S. Pat. No. 4,966,988, with diisobutyl aluminum hydride, followed by treating the intermediate aluminum-imine complex with (R)-1-(1-naphthyl)ethylamine, and reducing the intermediate imine with ethanolic sodium cyanoborohydride, according to the following Scheme 3:

These three processes however, require the use of reagents such as titanium isopropoxide which is highly hygroscopic and expensive, as well as toxic, and ethanolic or methanolic sodium cyanoborohydride, which is highly toxic and flammable, and not environmentally friendly, making the processes difficult to apply on industrial scale. In addition, the description of these processes is not detailed.

Moreover, the only synthetic route known for the precursor of the process described in Scheme 2, namely the 3-[3-(trifluoromethyl)phenyl]propionaldehyde (FMPP) is disclosed in footnote 12 of Tetrahedron Letters (2004) 45: 8355 and is described in Scheme 4:

Scheme 4

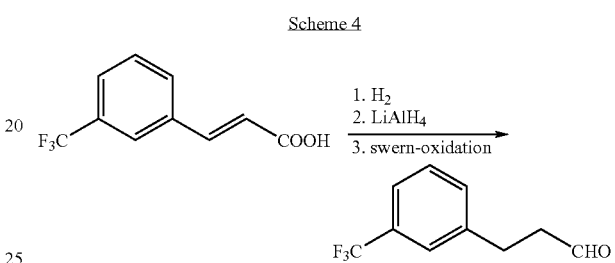

wherein reduction of the double bond of the corresponding Cinnamic acid derivative, followed by reduction of the carboxylic acid moiety to the corresponding alcohol, which is then oxidized to the aldehyde by Swern-oxidation. The Swern-oxidation reaction involves the use of reagents, such as oxalyl chloride and DMSO, which are not environmentally friendly and does not result in high yield, making the process arduous to apply on industrial scale.

Thus, an alternative process for the preparation of cinacalcet base and cinacalcet salt, which is more direct, higher

Scheme 3

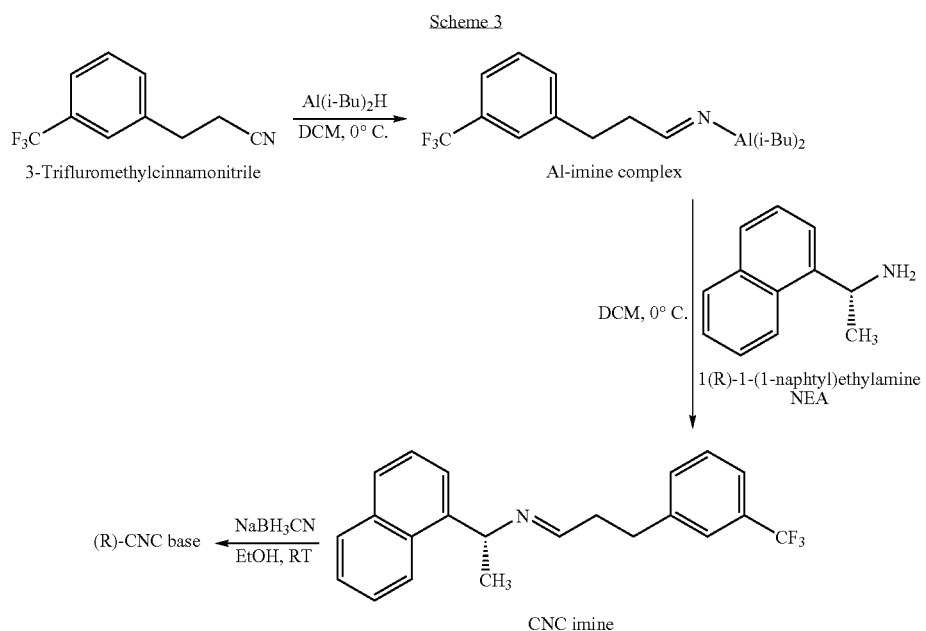

yield, environmental friendly and applicable to industrial scale production is desirable. The present invention provides such an alternative.

SUMMARY OF THE INVENTION

In a first embodiment, the present invention provides a process for preparing cinacalcet base from compound V, as illustrated in Scheme 5 comprising:
(a) converting the hydroxyl moiety of compound V into a good leaving group to obtain compound VI; and
(b) combining compound VI with (R)-1-Naphthylethylamine (herein R-NEA) and a base for at least a sufficient period to obtain cinacalcet base.

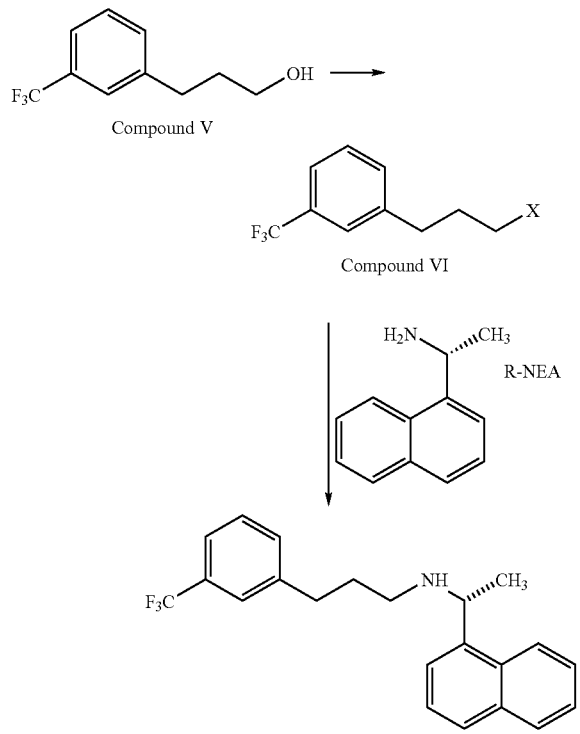

The process for conversion of the hydroxyl moiety of compound V into a good leaving group comprises combining a solution of compound V in an aprotic organic solvent selected from the group consisting of chlorinated aliphatic hydrocarbon, acetonitrile, $C_{2-6}$ ether and $C_{6-8}$ aromatic hydrocarbon with a reagent having a good leaving group to obtain a reaction mixture; and maintaining the reaction mixture at a temperature of about 0° C. to about 50° C., depending on the reagent, to obtain compound VI. Optionally, compound VI may be recovered.

The process of converting compound VI into cinacalcet base comprises combining a solution of compound VI in an organic solvent from a group consisting of $C_{6-8}$ aromatic hydrocarbon, $C_{1-4}$ alcohol, $C_{3-6}$ ester, $C_{3-6}$ ketone and acetonitrile or in a mixture of water and a $C_{6-8}$ aromatic hydrocarbon with (R)-1-Naphthylethylamine (herein R-NEA) in the presence of a base to obtain a reaction mixture and maintaining the reaction mixture at a temperature of about 50° C. to about 120° C. for at least a sufficient period to obtain cinacalcet base.

In a particularly preferred embodiment, a work-up method is presented for preparation of cinacalcet base substantially free of R-NEA, containing less than 0.2 area percent RNEA, preferably less than 0.1 area percent R-NEA comprising:
(a) providing a solution of cinacalcet base residue in a solvent in which cinacalcet base may dissolve;
(b) acidifying solution to obtain a pH of about 0 to 2;
(c) neutralizing the organic phase to obtain a pH of about 7 to about 8.5; and;
(d) recovering the substantially free of R-NEA cinacalcet base.

In another embodiment of the present invention, processes are presented for preparation of compound V from an intermediate or mixture of intermediates of cinacalcet selected from the group of compound IV, compound II, a mixture comprising compound IX and II; and a mixture comprising II and III, as illustrated in Schemes 6 and 7.

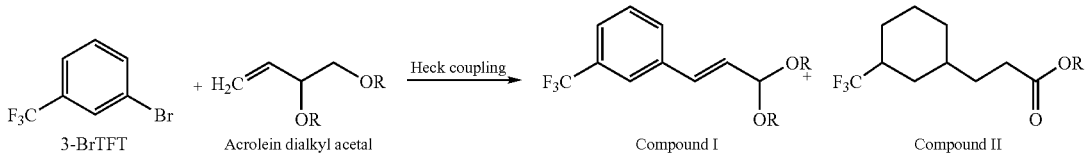

-continued
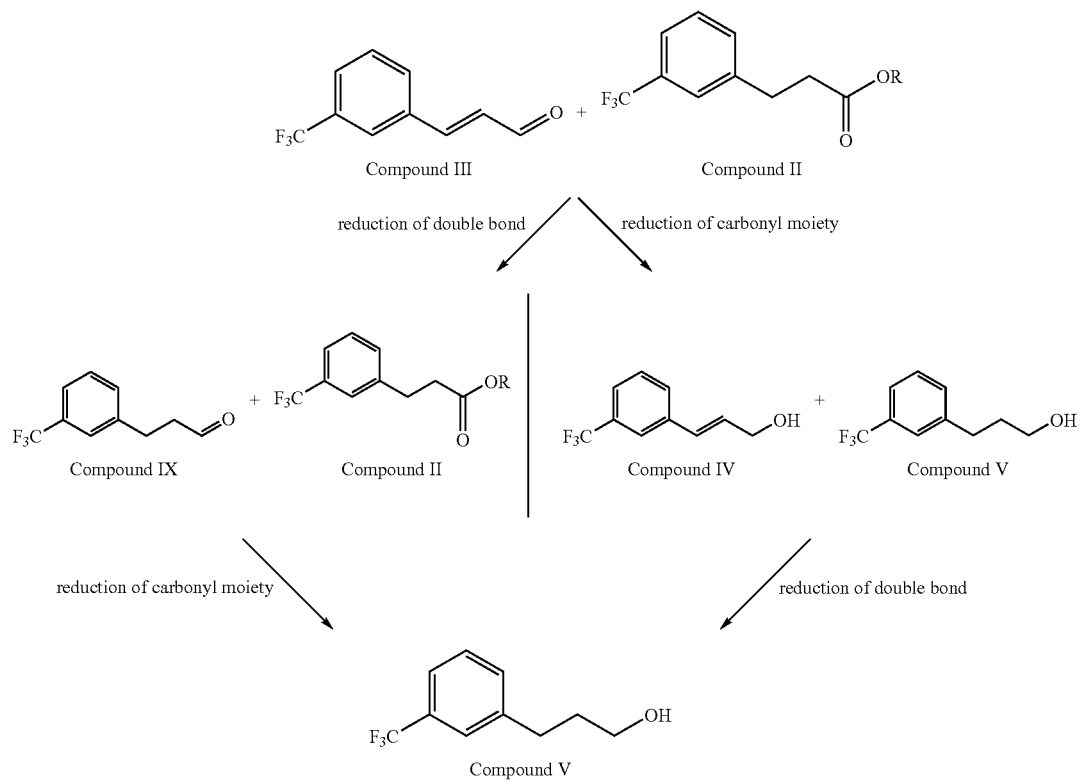
Scheme 7
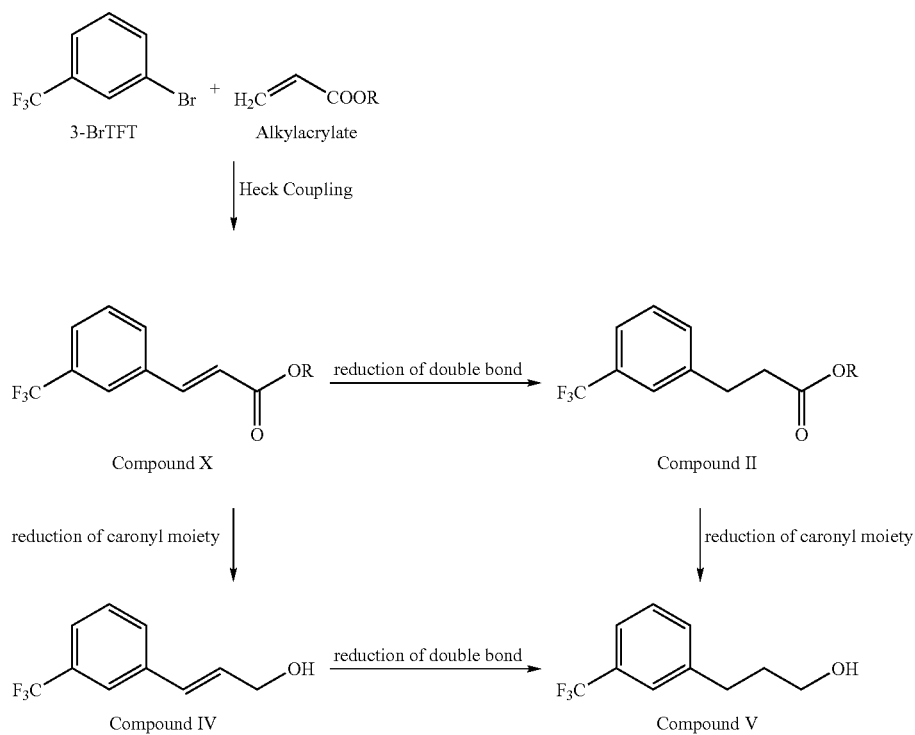

DETAILED DESCRIPTION OF THE INVENTION

The present invention presents an improved process for the preparation of cinacalcet intermediates and thereby improved processes for the preparation of cinacalcet free base, salts, crystalline forms, and solvates thereof. In particular, the process of the present invention provides a method which is most suitable for application on an industrial scale due to the more direct, high yield, main reaction and use of chemicals which are more environmentally friendly than prior art processes.

As used herein, an ambient temperature is meant to indicate a temperature of about 18° C. to about 25° C., preferably about 20° C. to about 22° C.

As used herein, compound I refers to 1-methyl-3-[(1E)-3-methylbut-1-enyl]benzene, as depicted in the following structure:

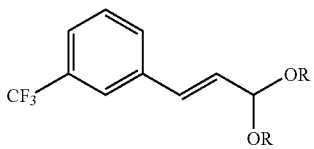

where R is a $C_1$ to $C_6$ aliphatic, branched or cyclic, bridged or unbridged alkyl.

As used herein, compound II refers to the following structure:

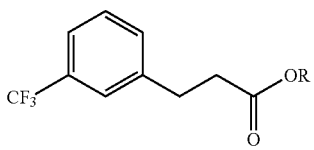

wherein R is a $C_1$ to $C_6$ aliphatic, branched or cyclic, bridged or unbridged alkyl.

As used herein, compound III refers to 2-propenal,3-[3-trifluoromethyl)phenyl], as depicted in the following structure:

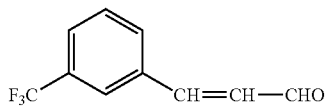

As used herein, compound IV refers to (2E)-3-[3-(trifluoromethyl)phenyl]prop-2-en-1-ol, as depicted in the following structure:

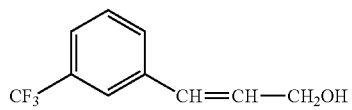

As used herein, compound V refers to 3-[3-(trifluoromethyl)phenyl]propan-1-ol, as depicted in the following structure:

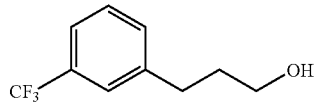

As used herein, compound VI refers to the following structure:

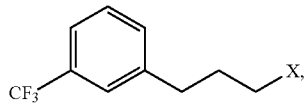

where X is $C_{1-3}$ alkyl sulfonate, substituted and non-substituted $C_{6-10}$ aryl sulfonate or halogen.

As used herein, compound IX refers to the following structure:

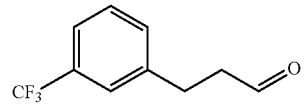

As used herein, compound X refers to the following structure:

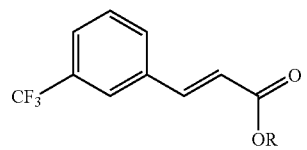

where R is a $C_1$ to $C_6$ aliphatic, branched or cyclic, bridged or unbridged alkyl.

As used herein, a good leaving group is defined as being the conjugate base of a strong acid. [For more on good leaving groups, see Streitwieser et al. (1976) *Introduction to Organic Chemistry* Ch8, pg 141]

The present invention provides processes that include Heck coupling reactions, generally known to one skilled in the art. [For more on Heck reactions, see Battistuzzi et. al. (2003) Organic letters 5(5), 777; Catalysis Letters, (2005) 102:281-284] This reaction is typically performed in a polar aprotic organic solvent, in the presence of a base and a metal catalyst to obtain a mixture. The mixture is then heated to a temperature of about 81° C. to about 145° C. for about 1 hour to about 10 hours. The polar aprotic organic solvent is preferably 1-methyl-2-pyrrolidinone (NMP), N,N-Dimethyl formamide (DMF), acetonitrile, mixtures thereof or with water. The preferred base is an ionic or non-ionic base, most preferably $K_2CO_3$, $Na_2CO_3$, KOAc, NaOAc and trialkyl amines such as $Et_3N$ (TEA) or $Bu_3N$ (TBA). The metal catalyst is palladium. The noble metal catalyst may be provided on an inert support such as carbon, activated carbon or alumina. Preferably, the noble metal catalyst is palladium on carbon ("Pd/C") in a form of extrudate or powder or $Pd(OAc)_2$. Optionally, the product may be recovered by conventional means known to one skilled in the art such as by evaporation or filtering.

The present invention provides processes which include reduction of a double bond, generally known to one skilled in the art. This reaction is typically performed in a polar organic solvent in the presence of a metal catalyst or Raney Nickel by bubbling hydrogen gas for a period of about 5 to about 24 hours to obtain the product. Optionally the product may be recovered. [For more on reduction of a double bond, see *Advanced Organic Chemistry* $2^{nd}$ Ed. Vol 1, 779-834.]

The present invention provides processes which include reduction of a carbonyl moiety, generally known to one skilled in the art. This reaction typically involves providing a starting material in an organic solvent such as a $C_{1-4}$ alcohol or $C_2$ to $C_6$ ether or mixtures such as a mixture of a water and a $C_{1-4}$ alcohol or a $C_2$ to $C_6$ ether with a $C_{1-4}$ alcohol in the presence of a reducing agent, to obtain a reaction mixture; and maintaining the reaction mixture at a suitable time and temperature, dependant on the reducing agent. Preferably, the reducing agent is a metal-hydride. The metal-hydride is preferably, sodium borohydride ($NaBH_4$), lithium borohydride ($LiBH_4$), calcium borohydride [$Ca(BH_4)_2$], lithium aluminum hydride ($LiAlH_4$) or complexes of $B_2H_6$ with THF, $Et_3N$ or $Me_2S$. The more preferred reducing agent is $LiAlH_4$. [For more on reduction of a carbonyl moiety, see *Synthetic Communications* (1982) 12(0), 463-467; *Modern Synthetic Reactions* (1972) W.A. Benjamin Inc., California]

When an ether is used as an organic solvent, diethylether or tetrahydrofuran are preferred. Methanol and ethanol are preferred alcohols. Preferably, the $C_{6-8}$ aromatic hydrocarbon is toluene. A preferred mixture is that of $C_{1-4}$ alcohol and water or that of THF and toluene. Depending on the reducing agent used, a suitable solvent is selected. For example, when the reducing reagent selected is sodium borohydride or lithium borohydride, the more preferred solvent is ethanol, while, when the reducing reagent is $LiAlH_4$, the preferred solvent is THF and the preferred mixture is that of an ether with a $C_{6-8}$ aromatic hydrocarbon, more preferably, that of THF and toluene. The reaction mixture is maintained at a specific time and temperature according to the reducing reagent used. Anyone skilled in the art will be able to determine appropriate time and temperature ranges. Generally, this temperature can be anywhere between about $-50°$ C. to about $50°$ C. For example, when the reducing reagent is $LiBH_4$ or $NaBH_4$, a preferred temperature is about $-40°$ C. to about ambient temperature, and a preferred time is about 16 to about 24 hours. However, when the reducing reagent is $LiAlH_4$, the preferred temperature is about $-20°$ C. to about $0°$ C., while the preferred time is about 1 to about 5 hours.

Optionally, the obtained product may be recovered by conventional means known in the art such as extraction, evaporation, filtering or distillations.

The present invention provides processes that include removal of protective group of an aldehyde (such as an acetyl group). This reaction is generally known to one skilled in the art. This reaction typically involves combining with an acid such as hydrochloride. [See Streitwieser et al. (1976) *Introduction to Organic Chemistry* Ch 15, 376.]

In a first embodiment, the present invention provides a process for preparing cinacalcet base from compound V, as illustrated in Scheme 5 comprising:
 (a) converting the hydroxyl moiety of compound V into a good leaving group to obtain compound VI; and
 (b) combining compound VI with (R)-1-Naphthylethylamine (herein R-NEA) and a base for at least a sufficient period to obtain cinacalcet base.

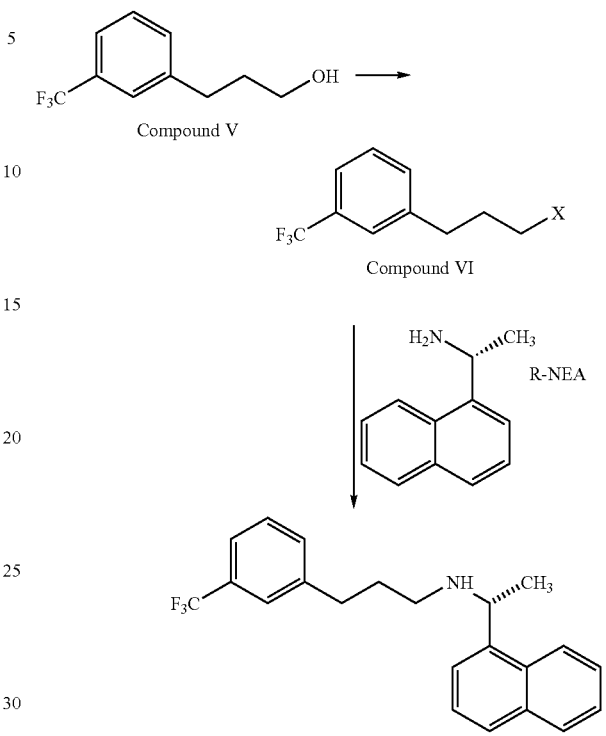

The process for conversion of the hydroxyl moiety of compound V into a good leaving group comprises combining a solution of compound V in an aprotic organic solvent selected from the group consisting of chlorinated aliphatic hydrocarbon, acetonitrile, $C_{2-6}$ ether and $C_{6-8}$ aromatic hydrocarbon with a reagent having a good leaving group to obtain a reaction mixture; and maintaining the reaction mixture at a temperature of about $0°$ C. to about $50°$ C., depending on the reagent, to obtain compound VI. Optionally, compound IV may be recovered.

Of the organic solvents, the preferred chlorinated aliphatic hydrocarbon is dichloromethane, the preferred ether is tetrahydrofuran and the preferred $C_{6-8}$ aromatic hydrocarbon is toluene. The more preferred organic solvent is toluene.

Preferably, the reagent containing the leaving group is selected from the group consisting of thionyl halide, aliphatic sulfonyl halide and aromatic sulfonyl halide. More preferably, the thionyl halide is either thionyl bromide or thionyl chloride, while the preferred aliphatic sulfonyl halide is methanesulfonyl chloride (herein MsCl) and the preferred aromatic sulfonyl halide is benzenesulfonyl chloride, 4-Nitrobenzenesulfonyl chloride (herein Nosyl chloride, NsCl) or p-toluenesulfonyl chloride (herein TsCl).

The most preferred reagent containing the leaving group is methanesulfonyl chloride. When the leaving group is a halogen such as chloride, a catalytic amount of KI or DMF is preferably added to the mixture.

Preferably, the reagent containing the leaving group is added to the solution of compound V in the organic solvent. More preferably, the reagent is added slowly in a drop-wise manner. Most preferably, this addition is while maintaining the reaction mixture at a temperature of about $0°$ C. to about $10°$ C.

Optionally, the reaction mixture contains a base. One skilled in the art will know when the base is necessary for the reaction. Preferably, the base is either an organic base or an inorganic base. Preferably, the organic base is an amine, more preferably, triethylamine, diisopropylethyl amine or other tertiary amines while the preferred inorganic base is an alkali carbonate, more preferably, $K_2CO_3$, $NaHCO_3$, $Na_2CO_3$ or $KHCO_3$. The more preferred base is triethylamine.

The sufficient period of time necessary for obtaining compound VI will depend on the parameters of the reaction. Preferably, maintaining the reaction mixture is for about is about 0.5 to about 24 hours. More preferably, the reaction mixture is maintained for about 0.5 hour to about 5 hours.

The crude compound VI may be recovered by any means known in the art and a skilled artisan will have little difficulty optimizing the parameters. In one example, the recovery may be by filtering, washing, and evaporation.

Preferably, the crude compound VI is used directly in the next stage without any purification process.

The process of converting compound VI into cinacalcet base comprises combining a solution of compound VI in an organic solvent from a group consisting of $C_{6-8}$ aromatic hydrocarbon, $C_{1-4}$ alcohol, $C_{3-6}$ ester, $C_{3-6}$ ketone and acetonitrile or in a mixture of water and a $C_{6-8}$ aromatic hydrocarbon with (R)-1-Naphthylethylamine (herein R-NEA) in the presence of a base to obtain a reaction mixture and maintaining the reaction mixture at a temperature of about 50° C. to about 120° C. for at least a sufficient period to obtain cinacalcet base.

Preferably, the $C_{6-8}$ aromatic hydrocarbon is toluene or acetonitrile with regard to both the mixture and the organic solvent. The preferred $C_{1-4}$ alcohol is ethanol or isopropylalcohol, the $C_{3-6}$ ester is EtOAc, and the preferred ketone is either methylisobutyl ketone (herein MIBK) or acetone. The most preferred solution of compound VI consists of compound IV and acetonitrile or a mixture of toluene and water.

The R-NEA may be obtained commercially. Preferably about 1 to about 1.5 molar equivalents relative to compound VI, are added, most preferably about 1 molar equivalent.

Preferably, the base is an inorganic base or an organic base. A preferred inorganic base is an alkali carbonate, more preferably, $K_2CO_3$, $Na_2CO_3$, $NaHCO_3$ or $KHCO_3$. A preferred organic base is an amine, more preferably, a tertiary amine, and most preferably tributylamine (herein TBA) or diisopropylethylamine. The most preferred base is $K_2CO_3$.

The reaction mixture is maintained, preferably at a temperature of about 70° C. to about 100° C. Preferably, the reaction time is about 5 to about 90 hours, more preferably about 21 to about 40 hours.

Optionally, a phase transfer catalyst can be added to the mixture while the mixture is being heated. Preferably, the phase transfer catalyst is tetrabutylamoinum bromide (TBAB). Optionally, water can be added to the reaction mixture in an amount of about 10% v/v of the reaction solvent.

Once cinacalcet base is obtained, it may be subsequently recovered by any means known to a skilled artisan such as by filtering off the salts obtained in the reaction and evaporating to obtain a residue.

In a particularly preferred embodiment, a work-up method is presented for preparation of cinacalcet base substantially free of R-NEA, containing less than 0.2 area percent RNEA, preferably less than 0.1 area percent R-NEA comprising:
(a) providing a solution of cinacalcet base residue in a solvent in which cinacalcet base may dissolve;
(b) acidifying solution to obtain a pH of about 0 to 2;
(c) neutralizing the organic phase to obtain a pH of about 7 to about 8.5; and;
(d) recovering the substantially free of R-NEA cinacalcet base.

Preferably, heating prior to step (b), to about 50° C. to about 80° C., is performed.

Preferably, the solvent is toluene, ethyl acetate, DCM or mixtures thereof. Preferably the solvent is in a sufficient amount to obtain a solution. For example, when toluene is used, about 5 to about 7 volumes per gram of residue would be suitable.

Preferably, acidifying is by addition of hydrochloric acid.

The pH is adjusted to about 8, preferably, by washing with about 1.5 volumes of water about 2 or 3 times, and then with two volumes of a saturated solution of $NaHCO_3$ (1×2 volumes per gram of residue after evaporation).

Recovering the cinacalcet base is then preferably by evaporation of the water miscible solvent, such as acetonitrile, alcohol, or acetone if present, washing with water (1×1.5 volumes per gram of residue after evaporation), and then evaporation under reduced pressure.

In another embodiment of the present invention, processes are presented for preparation of compound V from an intermediate or mixture of intermediates of cinacalcet selected from the group of compound IV, compound II, a mixture comprising compound IX and II; and a mixture comprising II and III, as illustrated in Schemes 6 and 7.

In one aspect of this embodiment, the present invention provides a process for preparing compound V by a reduction of double bond reaction of compound IV.

Preferably, compound IV is prepared from compound X or alternatively from a mixture of compound II and III. Preparation of compound IV from compound X is by reduction of the carbonyl moiety of compound X. This unsaturated ester of compound X may be prepared, for example, by a Heck-reaction of 1-bromo-3-(trifluoromethyl) benzene (herein 3-BrTFT) and alkylacrylate. Preferably, the alkylacrylate is ethylacrylate. Preparation of compound IV from a mixture of compound II and III is preferably by reduction of the carbonyl moiety of both compounds to obtain a mixture including compound IV and compound V. The mixture of the unsaturated alcohol of formula IV and the saturated alcohol of formula V may be recovered by conventional means known in the art such as extractions with an organic solvent selected from the group consisting of EtOAc, DCM and toluene, followed by separation of phases and evaporation of solvents. Preferably, the crude mixture of compound IV and compound V is used directly in the next step without the need for further purification. However, purification of the above mixture can be performed by means known in the art such as by distillation under a vacuum.

The mixture of compounds II and III can be provided by any means known to the skilled artisan, such as by a method described by U.S. Patent application. 2005/0234261 A1, Battistuzzi et al. (2003) *Organic letters* 5(5), 777 and Battistuzzi et al. *Synlett* (2003) 8: 1133. Preferably, the preparation of compound II and III is from the crude mixture compound I and compound II. The provided mixture of compound I and II are preferably prepared by a Heck coupling reaction of 3-BrTFT and acrolein dialkyl acetal.

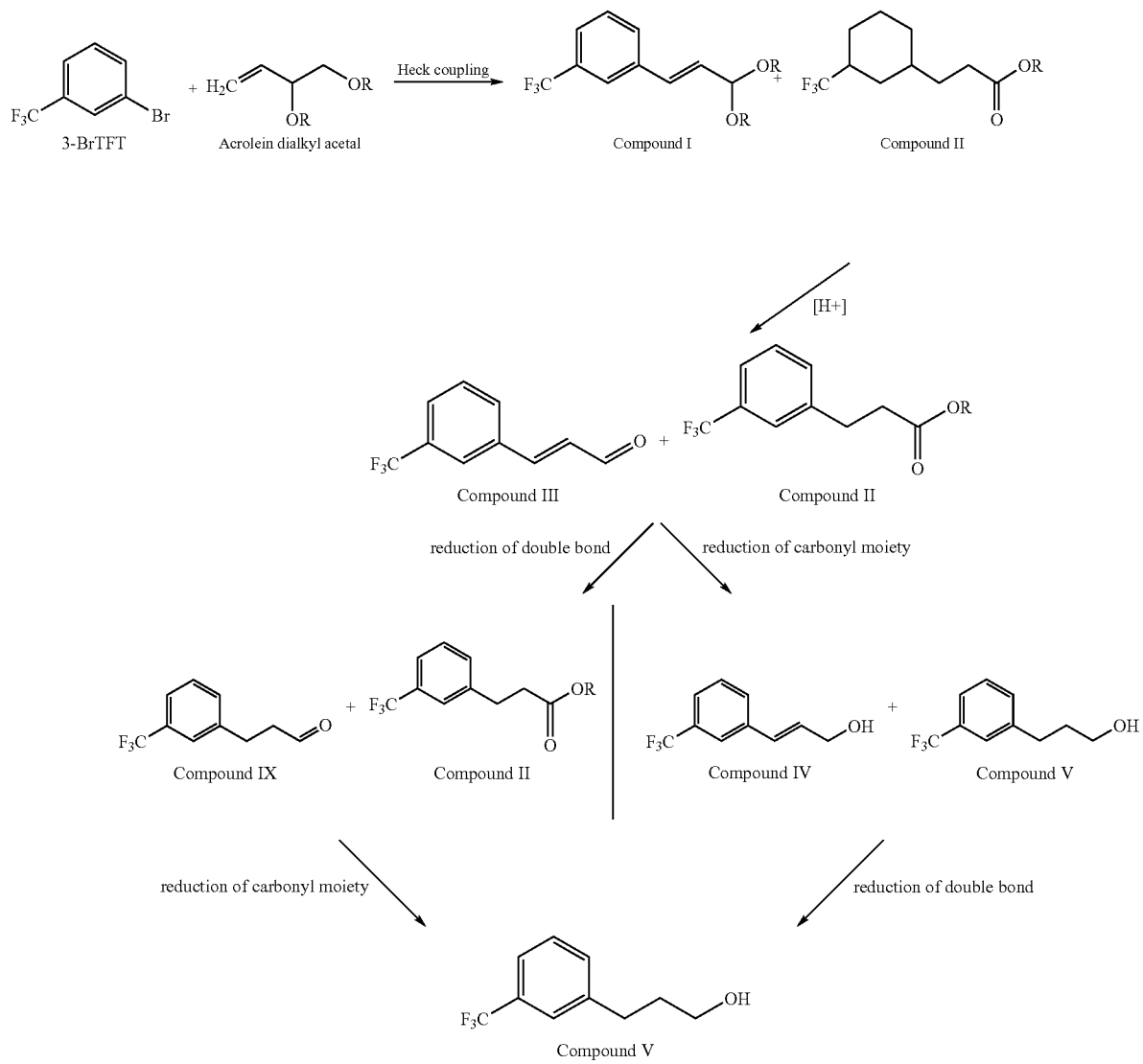
Scheme 6
In another aspect of this embodiment, the present invention provides a process for preparing compound V by a reduction of the carbonyl moiety of compound II. Preferably, compound II is prepared from compound X by a reduction of the double bond. Compound X is prepared as described above.ke
Scheme 7
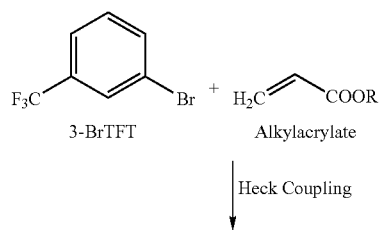

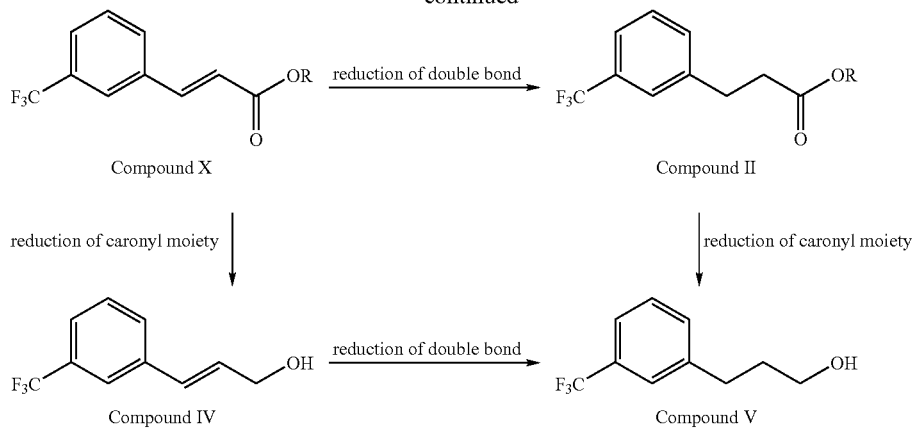

-continued

Compound X → reduction of double bond → Compound II reduction of carbonyl moiety ↓ ↓ reduction of carbonyl moiety Compound IV → reduction of double bond → Compound V In another aspect of this embodiment, the present invention provides a process for preparing compound V from a mixture of compound IX and II by a reduction of the carbonyl moiety.

Preferably, the mixture of IX and II is prepared by converting compound III to compound IX by reduction of the double bond, wherein the mixture throughout contains compound II. The mixture of compounds II and III can be provided by any means known to the skilled artisan, such as by a method described by U.S. Patent No. 2005/0234261 A1, Battistuzzi et. al. (2003) *Organic letters* 5(5), 777 and Battistuzzi et al. *Synlett* (2003) 8: 1133. Preferably, the preparation of compound II and III is from a mixture of compounds I and II. The provided mixture of compound I and II are preferably prepared by a Heck coupling reaction of 3-BrTFT and acrolein dialkyl acetal, as depicted in Scheme 6.

In another aspect of this embodiment, the present invention provides a process for the preparation of a mixture of compound V and IV is prepared from a mixture of compounds II and III through the reduction of the carbonyl moiety. The mixture of compound II and III can be provided by any means known to the skilled artisan, such as by a method described by U.S. Patent No. 2005/0234261 A1, Battistuzzi et. al. (2003) *Organic letters* 5(5), 777 and Battistuzzi et al. *Synlett* (2003) 8: 1133. Preferably, the preparation of compound II and III is from a mixture of compounds I and II. The provided mixture of compound I and II are preferably prepared by a Heck coupling reaction of 3-BrTFT and acrolein dialkyl acetal, as depicted in Scheme 6.

Instrumentation

| HPLC method for analyzing the R-NEA | |
|---|---|
| Column & packing | Hypersil GOLD 250 mm 4.6 mm 3μ C.N 25003-254630 |
| Eluent | 40% - 0.02 M $KH_2PO_4$ adjusted to pH = 6.0 with KOH 60% - Acetonitrile |
| Stop time: | 35 min |
| Flow: | 1.0 ml/min |
| Detector: | 210 nm. |
| Injection volume: | 10 μl. |
| Diluent: | 50% Water:50% ACN |
| Column temperature | Ambient |

EXAMPLES

The Heck Reaction

Preparation of a Mixture of Compounds I and II

Example 1

A 500 ml 3-necked flask equipped with a magnetic stirrer, a thermometer, a gas inlet adaptor and a reflux condenser was flushed with $N_2$ and charged with the following:

| Compound | moles | g | ml |
|---|---|---|---|
| 3-BrTFT | 0.15 | 33.75 | |
| AEA | 0.18 | | 27 |
| $K_2CO_3$ | | 14.46 | |
| NMP | | | 120 |
| Pd/C (2%) | $7.5 \times 10^{-4}$ | 3.97 | |

The reaction mixture was flushed with $N_2$ for 15 minutes and then heated to 140° C. for 2.5 hours. The reaction mixture was then cooled to room temperature and the catalyst and salts were filtered out. The cake was washed with 10 ml of NMP. The solvent was removed under reduced pressure (87° C./12 mmHg) to obtain a dark residue. Water (100 ml) or 1N HCl (20-30 ml) and Brine (50 ml) were added to the residue followed by addition of EtOAc (55 ml). Phase separation was done and the aqueous phase was extracted with EtOAc (55 ml) once again. The organic phase was dried over Sodium sulfate and filtered. The solvent was removed under vacuum to give 37.87 g of a mixture of unsaturated acetal (I) and ester (II) (ratio of 1:1.2 respectively).

Example 2

A 500 ml 3-necked flask equipped with a magnetic stirrer, a thermometer, a gas inlet adaptor and a reflux condenser was flushed with $N_2$ and charged with DMF (18 ml), 3-BrTFT (5.0 g, 1 eq), Acrolein diethyl acetal (3.5 g, 1.2 eq), $K_2CO_3$ (2.14 g, 0.7 eq) and Pd/$C_5$% (0.47 g). The reaction mixture was flushed with $N_2$ for 15 minutes and then heated to 125° C. for 5 hours. The reaction mixture was then cooled to room temperature and the catalyst and salts were filtered out. The cake was washed with 5 ml of DMF. The solvent was removed under reduced pressure (35° C./10 mmHg). 1N HCl (50 ml) was added to the residue and the mixture was stirred for 20 minutes at room temperature. Then EtOAc (50 ml) was added. Phase separation was done and the aqueous phase was extracted with EtOAc (50 ml) once again. The organic phase was dried over Sodium sulfate and filtered. The solvent was removed under reduced pressure to give 4.7 g of a mixture of unsaturated aldehyde (III) and ester (II).

Preparation of Compound X

Example 3

A 500 ml 3-necked flask equipped with a magnetic stirrer, a thermometer, a gas inlet adaptor and a reflux condenser is flushed with $N_2$ and charged with the following:

| Compound | moles | g | ml |
|---|---|---|---|
| 3-BrTFT | 0.15 | 33.75 | |
| Ethyl acrylate | 0.18 | 18.0 | |
| $K_2CO_3$ | | 14.46 | |
| NMP | | | 120 |
| Pd/C (2%) | $7.5 \times 10^{-4}$ | 3.97 | |

The reaction mixture is flushed with $N_2$ for 15 minutes and then heated to 140° C. for 2.5 hours. The reaction mixture is then cooled to room temperature and the catalyst and salts are filtered out. The cake is washed with 10 ml of NMP. The solvent is removed under reduced pressure (87° C./12 mmHg) to obtain a dark residue. Water (100 ml) or 1N HCl (20-30 ml) and Brine (50 ml) are added to the residue followed by addition of EtOAc (55 ml). Phase separation is done and the aqueous phase is extracted with EtOAc (55 ml) once again. The organic phase is dried over Sodium sulfate and filtered. The solvent is removed under vacuum to give unsaturated ester (X).

Example 4

A 500 ml 3-necked flask equipped with a magnetic stirrer, a thermometer, a gas inlet adaptor and a reflux condenser is flushed with $N_2$ and charged with DMF (18 ml), 3-BrTFT (5.0 g, 1 eq), Ethyl acrylate (2.7 g, 1.2 eq), $K_2CO_3$ (2.14 g, 0.7 eq) and Pd/C 5% (0.47 g). The reaction mixture is flushed with $N_2$ for 15 minutes and then heated to 125° C. for 5 hours. The reaction mixture is then cooled to room temperature and the catalyst and salts are filtered out. The cake is washed with 5 ml of DMF. The solvent is removed under reduced pressure (35° C./10 mmHg). Then EtOAc (50 ml), water (100 ml) and Brine (50 ml) are added. Phase separation is done and the aqueous phase is extracted with EtOAc (50 ml) once again. The organic phase is dried over Sodium sulfate and filtered. The solvent is removed under reduced pressure to give unsaturated ester (X).

The Hydrolysis Reaction

Preparation of a Mixture of Compounds II and III

Example 5

10 g of a mixture of unsaturated acetal (I) and ester (II) (crude material of stage 1) were stirred in 1N Hydrochloric acid at room temperature for 3 hours. EtOAc (50 ml) was added. Phase separation was done. The organic phase was dried over Sodium sulfate and the solvent was evaporated under reduced pressure to give 8.17 g of a mixture of unsaturated aldehyde (III) and ester (II) as a brown oil.

Example 6 (One Pot)

A 12 L reactor equipped with a mechanical stirrer, a thermometer, a gas inlet adaptor and a reflux condenser is flushed with nitrogen and charged with DMF (8.1 L), 3-BrTFT (1.38 L, 1 eq), Acrolein diethyl acetal (1.8 L, 1.2 eq), $K_2CO_3$ (1.0 Kg, 0.7 eq) and Pd/C 5% (44.6 g). The reaction mixture is flushed with nitrogen for 15 minutes and then heated to 130° C. for 5 hours. The reaction mixture is then cooled to room temperature and the catalyst and salts are filtered out. The cake is washed with 500 ml of DMF. The solvent is removed under reduced pressure (65° C./10 mmHg). 1N HCl (3.4 L) is added to the residue and the mixture is stirred for 1 hour at room temperature. Then Toluene (3.4 L) is added. Phase separation is done and the aqueous phase is discarded. The organic phase is wash with Brine (3.4 L) and water (3.4 L). An azeotropic distillation of water/Toluene was performed under reduced pressure to give 4.95 liter of a mixture of unsaturated aldehyde (III) and ester (II).

Reduction of Carbonyl Group Reaction

Preparation of the Mixture of Compounds IV and V

Example 7

8.17 g of a mixture of unsaturated aldehyde (III) and ester (II) were dissolved in Ethanol (95%, 70 ml). Sodium borohydride (3.12 g) was added to the solution. The reaction mixture was stirred at room temperature for 24 hours. Then water (130 ml), Brine (30 ml) and EtOAc (70 ml) were added. Phase separation was done and the organic phase was dried over Sodium sulfate. After filtration, the solvent was removed under vacuum to give 3.41 g of a mixture of unsaturated alcohol (IV) and saturated alcohol (V).

Preparation of Compound IV

Example 8

10 g of saturated ester (II) is dissolved in Ethanol (95%, 70 ml). Sodium borohydride (1.5 eq) is added to the solution. The reaction mixture is stirred at room temperature for 24 hours. Then water (130 ml), Brine (30 ml) and EtOAc (70 ml) are added. Phase separation is done and the organic phase is dried over Sodium sulfate. After filtration the solvent is removed under vacuum to give saturated alcohol (V).

Preparation of the Compound IV

Example 9

10 g of unsaturated ester (X) is dissolved in Ethanol (95%, 70 ml). Sodium borohydride (1.5 eq) is added to the solution. The reaction mixture is stirred at room temperature for 24 hours. Then water (130 ml), Brine (30 ml) and EtOAc (70 ml) are added. Phase separation is done and the organic phase is dried over Sodium sulfate. After filtration the solvent is removed under vacuum to give unsaturated alcohol (IV).

Preparation of the Mixture of IX and II

Example 10

8.2 g of a mixture of saturated aldehyde (IX) and saturated ester (II) is dissolved in Ethanol (95%, 70 ml). Sodium borohydride (3.12 g) is added to the solution. The reaction mixture is stirred at room temperature for 24 hours. Then water (130 ml), Brine (30 ml) and EtOAc (70 ml) are added. Phase separation is done and the organic phase is dried over Sodium sulfate. After filtration the solvent is removed under vacuum to give saturated alcohol (V).

Preparation of the Mixture of IV and V

Example 11

10.0 g of a mixture of unsaturated aldehyde (III) and saturated ester (II) was dissolved in THF (40 ml). The mixture was cooled to (−5° C.) and 1M solution of LAH in THF (17.5 ml, 0.42 eq) was added drop-wise while the temperature of the reaction maintained at (−5° C.). The mixture was stirred for additional 40 minutes at the same temperature. Acetone (2.5 ml) was added drop-wise. Then aqueous solution of $H_2SO_4$ (66%, 10 ml) was added drop-wise. The obtained precipitate was filtered out. Toluene (80 ml) and Brine (80 ml) were added to the filtrate (THF solution). Phase separation was done. The organic phase was washed with water (80 ml) and the solvent was evaporated until dryness to give 8.2 g of crude mixture of unsaturated alcohol (IV) and saturated alcohol (V). Further purification can be done by distillation of the obtained mixture at 63-70° C./LT 1 mbar.

Preparation of the Mixture of IV and V

Example 12

10.0 g of a mixture of unsaturated aldehyde (III) and saturated ester (II) was dissolved in THF (40 ml). The mixture was cooled to (−5° C.) and 1M solution of LAH in THF (17.5 ml, 0.42 eq) was added drop-wise while the temperature of the reaction maintained at (−5° C.). The mixture was stirred for additional 40 minutes at the same temperature. Acetone (2.5 ml) was added drop-wise. Then aqueous solution of NaOH (22%, 10 ml) was added drop-wise. The obtained precipitate was filtered out. The filtrate (THF solution) was washed with Brine (1×80 ml) and water (3×80 ml) to obtain pH 7. The solvent was then evaporated until dryness to give 7.2 g of crude mixture of unsaturated alcohol (IV) and saturated alcohol (V). Further purification can be done by distillation of the obtained mixture at 63-70° C./LT 1 mbar.

Example 13

2.72 L (1.2 Kg) of a mixture of unsaturated aldehyde (III) and ester (II) was cooled in a 10 L reactor to (−10° C.)-(−20° C.). LiAlH$_4$ 1M solution in THF (2.1 L) was added drop-wise. The reaction mixture was treated with Acetone (250 ml) and then with 5% $H_2SO_4$ (2.5 L). Phase separation was done and the organic phase was washed once more with 5% $H_2SO_4$ (2.5 L), Brine (2.0 L) and water (2.0 L). The solvent was distilled out at 70° C./25 mbar to give a mixture of unsaturated alcohol (IV) and saturated alcohol (V).

Hydrogenation Reactions

Preparation of the Compound V

Example 14

An ethanolic solution of a mixture of the compounds IV and V (3.41 g in 30 ml of Ethanol) was hydrogenated (1 atm. of $H_2$) in the presence of palladium on carbon (10% w/w of starting material) for 16 hours at room temperature. Then the catalyst was filtered out and the solvent was evaporated to dryness to obtain saturated alcohol (V).

Example 15

A mixture of unsaturated alcohol (IV) and saturated alcohol (V) was further purified by high vacuum distillation at 140° C./mbar to give 1.4 Kg of the above mixture containing 13% (% on area by HPLC) of unsaturated alcohol (IV) and 87% (% on area by HPLC) of saturated alcohol (V).

Preparation of the Mixture of II and IX

Example 16

An ethanolic solution of a mixture of unsaturated aldehyde (III) and saturated ester (II) (3.5 g in 30 ml of Ethanol) is hydrogenated (1 atm. of $H_2$) in the presence of palladium on carbon (10% w/w of starting material) for 16 hours at room temperature. Then the catalyst is filtered out and the solvent is evaporated to dryness to give a mixture of saturated aldehyde (IX) and saturated ester (II).

Preparation of the Compound V

Example 17

An ethanolic solution of unsaturated alcohol (IV) (3.5 g in 30 ml of Ethanol) is hydrogenated (1 atm. of $H_2$) in the presence of palladium on carbon (10% w/w of starting material) for 16 hours at room temperature. Then the catalyst is filtered out and the solvent is evaporated to dryness to give saturated alcohol (V).

Preparation of the Compound V

Example 18

An ethanolic solution of unsaturated ester (X) (3.5 g in 30 ml of Ethanol) is hydrogenated (1 atm. of $H_2$) in the presence of palladium on carbon (10% w/w of starting material) for 16 hours at room temperature. Then the catalyst is filtered out and the solvent is evaporated to dryness to give saturated ester (II).

Conversion of OH to a Good Leaving Group

Preparation of the Compound VI

Example 19

8.0 g of saturated alcohol (V) were dissolved in THF or Toluene (40 ml). A catalytic amount of DMF (0.3 ml) was added to the solution. Thionyl Chloride ($SOCl_2$) (3.2 ml) was added drop-wise at room temperature. The reaction mixture was heated to 45° C. for 20 hours. The solvents and traces of $SOCl_2$ were evaporated under reduced pressure to give 9.5 g of the crude chloride derivative (VI). The crude material may be purified by vacuum distillation (80-87° C./2 mmHg).

Example 20

3.0 g of crude material of compound V were dissolved in DCM (60 ml). TEA (5.6 ml) was added followed by drop-wise addition of Methanesulfonyl chloride (1.2 ml) at room temperature. The reaction mixture was stirred at room temperature for 2 hours. Then the reaction mixture was poured into crushed ice (98 g) and 1NHCl (30 ml). DCM (30 ml) was added to the mixture. Phase separation was done and the aqueous phase was extracted with DCM (30 ml) once again. The organic phase was dried over Sodium sulfate and the solvent was evaporated under vacuum to give 3.39 g of the compound VI.

Example 21

A 10 liter glass stirred reactor was flushed with nitrogen. The nitrogen blanketing continued during the reaction, and was stopped when the work-up was started. 600 g of compound V, 3.6 liter of Toluene and 492 ml of triethyl amine were charged into the reactor at room temperature. The stirrer was turned on, and then the reactor content was cooled to 4.5° C. 255.6 ml of Mesyl chloride (MsCl) was charged drop-wise during 50 minutes, while cooling the reactor. The reactor was heated to 25° C., and the triethyl amine salt (TEA HCl) was filtered under reduced pressure, and then the filter cake was washed with 1.8 liter of Toluene (3×600 ml). The organic phase was washed with 500 ml of 0.2N HCl, then the phases were separated, and the organic phase was washed with water (3×1.2 L) to achieve pH=7. Toluene was evaporated under reduced pressure. After completion of the evaporation, 1.2 liter of fresh Toluene was charged into the reactor, and the solvent was evaporated at similar conditions. 858 g of compound VI were obtained.

Preparation of Cinacalcet Base

Example 22

1.7 g of compound VI were dissolved in Acetonitrile (30 ml). (R)-1-Naphtylethyl amine (1.03 g) and anhydrous $K_2CO_3$ (1.66 g) were added and the reaction mixture was heated to reflux temperature for 7 hours. Then salts were filtered out and the solvent was removed under reduced pressure to give 2.4 g of crude Cinacalcet base. The crude product was purified by column chromatography on silica gel using a gradient from Dichloromethane to a mixture of 2.5-5% Methanol/97.5-95% Dichloromethane as eluent.

Example 23

2.2 g of chloride (VI) were dissolved in Acetonitrile (17.5 ml). (R)-1-Naphtylethyl amine (1.5 ml) and anhydrous $K_2CO_3$ (2.7 g) were added and the reaction mixture was heated to reflux temperature for 5 hours. Potassium iodide (230 mg) was added and the reaction mixture was stirred at reflux for additional 19 hours. Then salts were filtered out and the solvent was removed under reduced pressure. The residue was dissolved in DCM (16 ml). The obtained solution was washed with 5% aqueous HCl solution (1×17 ml), saturated solution of $NaHCO_3$ (1×16 ml) and finally with water (2×16 ml). The organic phase was dried over $Na_2SO_4$, filtered and the solvent was evaporated until dryness to obtain 1.6 g of Cinacalcet base.

Example 24

25.5 g of compound VI were dissolved in Acetonitrile (204 ml). (R)-1-Naphtylethyl amine (14.5 ml) and anhydrous $K_2CO_3$ (24.9 g) were added and the reaction mixture was heated to reflux temperature for 16 hours. Then salts were filtered out and the solvent was removed under reduced pressure. The residue was dissolved in DCM (75 ml). The obtained solution was washed with 5% aqueous HCl solution (pH=1), saturated solution of $NaHCO_3$ (pH=8-9) and finally with water. The organic phase was dried over $Na_2SO_4$, filtered and the solvent was evaporated until dryness to obtain 33.4 g of Cinacalcet base.

Example 25

25.5 g of compound VI were dissolved in Acetonitrile (204 ml). (R)-1-Naphtylethyl amine (14.5 ml) and anhydrous $K_2CO_3$ (24.9 g) were added and the reaction mixture was heated to reflux temperature for 16 hours. Then salts were filtered out and the solvent was removed under reduced pressure. The residue was dissolved in ethyl acetate (75 ml). The obtained solution was washed with 5% aqueous HCl solution (pH=1), saturated solution of $NaHCO_3$ (pH=8-9) and finally with water. The organic phase was dried over $Na_2SO_4$, filtered and the solvent was evaporated until dryness to obtain 33.4 g of Cinacalcet base.

Example 26

25.5 g of compound VI were dissolved in Acetonitrile (204 ml). (R)-1-Naphtylethyl amine (14.5 ml) and anhydrous $K_2CO_3$ (24.9 g) were added and the reaction mixture was heated to reflux temperature for 16 hours. Then salts were filtered out and the solvent was removed under reduced pressure. The residue was dissolved in toluene (75 ml). The obtained solution was washed with 5% aqueous HCl solution (pH=1), saturated solution of $NaHCO_3$ (pH=8-9) and finally with water. The organic phase was dried over $Na_2SO_4$, filtered and the solvent was evaporated until dryness to obtain 33.4 g of Cinacalcet base.

Example 27

25.5 g of compound VI were dissolved in Acetonitrile (204 ml). (R)-1-Naphtylethyl amine (14.5 ml) and anhydrous $K_2CO_3$ (24.9 g) were added and the reaction mixture was heated to reflux temperature for 16 hours. Then salts were filtered out and the solvent was removed under reduced pressure. The residue was dissolved in DCM (75 ml). The obtained solution was washed with 5% aqueous HCl solution (pH=1), saturated solution of $NaHCO_3$ (pH=8-9) and finally with water. The organic phase was dried over $Na_2SO_4$, filtered and the solvent was evaporated until dryness to obtain 33.4 g of Cinacalcet base. No further purification by column chromatography was needed.

Example 28

25.5 g of compound VI were dissolved in Acetonitrile (204 ml). (R)-1-Naphtylethyl amine (14.5 ml) and anhydrous $K_2CO_3$ (24.9 g) were added and the reaction mixture was heated to reflux temperature for 16 hours. Then salts were filtered out and the solvent was removed under reduced pressure. The residue was dissolved in DCM (75 ml). The obtained solution was washed with 5% aqueous HCl solution (pH=1), saturated solution of $NaHCO_3$ (pH=8-9) and finally with water. The organic phase was dried over $Na_2SO_4$, filtered and the solvent was evaporated until dryness to obtain 33.4 g of Cinacalcet base.

Example 29

10.0 g of compound VI (1 eq) were dissolved in Toluene (60 ml). (R)-1-Naphtylethyl amine (0.98 eq) and anhydrous $K_2CO_3$ (2 eq) were added and the reaction mixture was heated to reflux temperature for 14 hours. Then salts were filtered out and the solvent was removed under reduced pressure. The residue was dissolved in DCM (75 ml). The obtained solution was washed with 5% aqueous HCl solution (pH=1), saturated solution of NaHCO$_3$ (pH=8-9) and finally with water. The organic phase was dried over Na$_2$SO$_4$, filtered and the solvent was evaporated until dryness to obtain 11.0 g of Cinacalcet base.

Example 30

5.0 g of compound VI (1 eq) were dissolved in Toluene (80 ml). (R)-1-Naphtylethyl amine (0.98 eq) and anhydrous K$_2$CO$_3$ (2 eq) were added and the reaction mixture was heated to 80° C. for 12 hours. Then Tetrabutyl ammonium bromide (TBAB) (5% per moles of (VI)) was added. The mixture was heated for additional hour at 80° C. Salts were filtered out and the solvent was removed under reduced pressure. The residue was dissolved in DCM (75 ml). The obtained solution was washed with 5% aqueous HCl solution (pH=1), saturated solution of NaHCO$_3$ (pH=8-9) and finally with water. The organic phase was dried over Na$_2$SO$_4$, filtered and the solvent was evaporated until dryness to obtain of Cinacalcet base.

Preparation Cinacalcet Base, Substantially Pure of RNEA

Example 31

5.0 g of compound VI were dissolved in Acetonitrile (20 ml). (R)-1-Naphtylethyl amine (R-NEA) (1 eq) and anhydrous K$_2$CO$_3$ (1 eq) were added and the reaction mixture was heated to reflux temperature for 22 hours. Then salts were filtered out and the solvent was removed under reduced pressure. The residue was dissolved in Toluene or Ethyl acetate (7 volumes per gram of residue after evaporation). The obtained solution was heated to 70° C. and 32% HCl (2 volumes per gram of residue after evaporation) was added to obtain pH=0-1. The organic phase was then washed with water (2-3×1.5 volumes per gram of residue after evaporation), saturated solution of NaHCO$_3$ (1×2 volumes per gram of residue after evaporation) to obtain pH=8, and finally with water (1×1.5 volumes per gram of residue after evaporation). The solvent (Toluene or Ethyl acetate) was then evaporated under reduced pressure until dryness to give Cinacalcet free base, less than 0.1% R-NEA Example 32

Compound VI (10 g, 1 eq) and (R)-1-Naphtylethyl amine (R-NEA) (4.7 ml, 1 eq) were dissolved in Toluene (20 ml, 2 vol.). K$_2$CO$_3$ (4 g, 1 eq) was dissolved in distilled H$_2$O (20 ml, 2 vol.) and the obtained solution was added under N$_2$ to the toluenic solution of Compound VI and R-NEA. The reaction mixture was heated to reflux temperature (85° C.) for 20 hours. Then it was cooled to room temperature and phase separation was done. The organic phase was heated to 70° C. and the obtained solution was washed with 10% aqueous HCl solution (2×10 ml) (pH=0), saturated solution of NaHCO$_3$ (1×20 ml) (pH=8-9) and finally with water (pH=7). The solvent was evaporated under reduced pressure until dryness to give Cinacalcet base.

One Pot Preparation Cinacalcet Base, Substantially Pure of RNEA

Example 33

A 10 liter glass stirred reactor was flushed with nitrogen at low flow rate. The nitrogen blanketing continued during the reaction, and was stopped when the work-up was started. 820 g of compound V, 3 liter of Acetonitrile, 367.5 g of K$_2$CO$_3$ and 455.6 g of R-Naphtylethyl amine (R-NEA) were charged into the reactor at room temperature. The stirrer was turned on, then the reactor was heated to reflux temperature (81.7° C.) and stirred at this temperature for 22 hours. The reactor was cooled to 50° C. and the salts were filtered out under reduced pressure. The filter cake was washed with Acetonitrile (4×750 ml). The reactor was cooled to 20° C. and the Acetonitrile was evaporated under reduced pressure. The reactor was cooled to 10° C., and 5.25 L of Toluene were charged into the reactor. The reactor was heated to 70° C., and 1.78 L of 32% aq HCl solution were charged during 50 minutes. The reactor was stirred for 15 minutes, and then the acidic aqueous phase was separated. The organic phase was washed with water (3×1340 ml), then with saturated Sodium bicarbonate (2×1781 ml). Finally, the organic phase was washed with water. The Toluene was evaporated under reduced pressure to obtain 886 g of Cinacalcet base.

What is claimed is:

1. A process for preparing cinacalcet base, comprising: providing compound V of the structure:

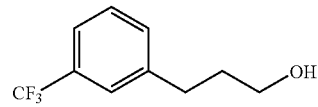

converting the hydroxyl moiety of compound V into a good leaving group wherein a good leaving group is a conjugate base to obtain compound VI of the structure:

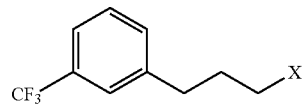

and combining compound VI with (R)-1-Naphthylethylamine (NEA) in the presence of a base at a temperature of about 50° C. to about 120° C. to obtain cinacalcet base.

2. The process of claim 1, wherein the conversion of the hydroxyl moiety of compound V into a good leaving group comprises:

(a) combining a solution of compound V in an aprotic organic solvent selected from the group consisting of chlorinated aliphatic hydrocarbon, acetonitrile, a C$_{2-6}$ ether and a C$_{6-8}$ aromatic hydrocarbon, with a reagent having a good leaving group to obtain a reaction mixture; and (b) maintaining the reaction mixture at a temperature of about 0° C. to about 50° C. to obtain compound VI.

3. The process of claim 2, wherein the aprotic organic solvent is selected from the group consisting of dichloromethane, tetrahydrofuran, and toluene.

4. The process of claim 3, wherein the aprotic organic solvent is toluene.

5. The process of claim 2, wherein the reagent is selected from the group consisting of thionyl halide, aliphatic sulfonyl halide and aromatic sulfonyl halide.

6. The process of claim 5, where the reagent is selected from the group consisting of thionyl bromide, thionyl chloride, methanesulfonyl chloride (MsCl), benzenesulfonyl chloride, 4-Nitrobenzenesulfonyl chloride (NsCl), and p-toluenesulfonyl chloride (TsCl).

7. The process of claim 6, wherein the reagent is methanesulfonyl chloride.

8. The process of claim 2, wherein the reagent is gradually added to the solution containing compound V.

9. The process of claim 2, wherein the reagent is gradually added at a temperature of about 0° C. to about 10° C.

10. The process of claim 2, wherein the reaction mixture contains an organic or inorganic base.

11. The process of claim 10, wherein the organic or inorganic base is selected from the group consisting of an amine or alkali carbonate.

12. The process of claim 11, wherein the amine or alkali carbonate is selected from the group consisting of triethylamine, diisopropylethyl amine, tertiary amine, $K_2CO_3$, $NaHCO_3$, $Na_2CO_3$, and $KHCO_3$.

13. The process of claim 12, wherein the base is triethylamine.

14. The process of claim 2, wherein the reaction mixture is maintained for about 0.5 to about 24 hours.

15. The process of claim 14, wherein the reaction mixture is maintained for about 0.5 hour to about 5 hours.

16. The process of claim 1, wherein compound VI is present as a solution in an organic solvent selected from the group consisting of $C_{6-8}$ aromatic hydrocarbon, $C_{1-4}$ alcohol, $C_{3-6}$ ester, $C_{3-6}$ ketone, and acetonitrile or a mixture of water and a $C_{6-8}$ aromatic hydrocarbon.

17. The process of claim 16, wherein the organic solvent is selected from the group consisting of toluene, ethanol, isopropylalcohol, EtOAc methylisobutyl ketone (MIBK), acetone, and acetonitrile.

18. The process in claim 16, wherein compound VI is present as a solution in acetonitrile or a mixture of water and toluene.

19. The process of claim 1, wherein the (R)-1-Naphthylethylamine is present in an amount of about 1 to about 1.5 molar equivalents relative to compound VI.

20. The process of claim 1, wherein the base is selected from the group consisting of alkali carbonates and amines.

21. The process of claim 20, wherein the base is a tertiary amine.

22. The process of claim 20, wherein the base is selected from the group consisting of $K_2CO_3$, $Na_2CO_3$, $NaHCO_3$, $KHCO_3$, tributylamine (TBA), and diisopropylethylamine.

23. The process of claim 20, wherein the base is $K_2CO_3$.

24. The process of claim 1, wherein the base is added to the solution of compound VI and (R)-1-Naphthylethylamine.

25. The process of claim 1, wherein the compound VI and (R)-1-Naphthylethylamine are combined at a temperature of about 70° C. to about 100° C.

26. The process of claim 1, wherein combining is for about 5 to about 90 hours.

27. The process of claim 26, wherein combining is for about 21 to 40 hours.

28. The process of claim 1, wherein a phase transfer catalyst is admixed during the combination of the compound VI and (R)-1-Naphthylethylamine.

29. The process in claim 28, wherein the phase transfer catalyst is tetrabutylamoinum bromide (TBAB).

30. The process in claim 16, which further comprises recovering cinacalcet base residue by filtering and evaporating solvent.

31. The process in claim 16, wherein cinacalcet base having less than 0.2 area percent (R)-1-Naphthylethylamine is prepared in a process comprising:

(a) providing a solution of cinacalcet base contaminated with (R)-1-Naphthylethylamine in a solvent in which cinacalcet base dissolves;

(b) acidifying the solution to obtain a pH of about 0 to 2;

(c) neutralizing the organic phase to obtain a pH of about 7 to about 8.5; and (d) recovering cinacalcet base containing less than 0.2 area percent (R)-1-Naphthylethylamine.

32. The process in claim 31, wherein the cinacalcet base contains less than 0.1 area percent of (R)-1-Naphthylethylamine.

33. The process in claim 31, wherein, prior to step (b), heating to about 50° C. to about 80° C. is performed.

34. The process of claim 31, wherein the solution of cinacalcet base comprises a solvent selected from the group consisting of toluene, ethyl acetate, DCM, and mixtures thereof.

35. The process of claim 31, wherein the solvent is present in a amount sufficient to obtain a solution.

36. The process of claim 31, wherein acidifying the solution is by addition of hydrochloric acid.

37. The process of claim 31, wherein neutralizing is by washing with a saturated solution of $NaHCO_3$, and then washing with water.

38. The process of claim 37, wherein recovering cinacalcet free base substantially free of (R)-1-Naphthylethylamine is by evaporation of the excess solvent.

39. The process of claim 1, wherein the compound V is prepared from compound II of the following structure, where R is a $C_1$ to $C_6$ aliphatic, branched or cyclic, bridged or unbridged alkyl:

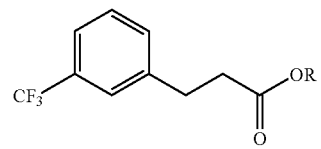

by the reduction of the carbonyl moiety of compound II.

40. The process of claim 39, wherein compound II is prepared from compound X of the following structure, where R is a $C_1$ to $C_6$ aliphatic, branched or cyclic, bridged or unbridged alkyl:

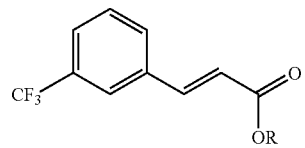

by reduction of a carbonyl.

41. The process of claim 1, wherein the compound V is prepared from compound IV, (2E)-3-[3-(trifluoromethyl)phenyl]prop-2-en-1-ol,

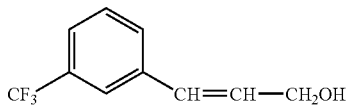

by reduction of the double bond of compound IV.

42. The process of claim 41, wherein compound IV is prepared from compound X by reduction of a carbonyl.

43. The process of claim 1, wherein the compound V is prepared as a mixture of compound V and IV from a mixture of compounds II and III, wherein compound III is 2-propenal,3-[3-trifluoromethyl)phenyl], having the following structure:

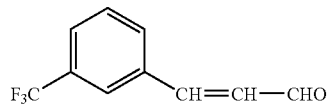

by reduction of the carbonyl wherein compounds II and IV are as follows:

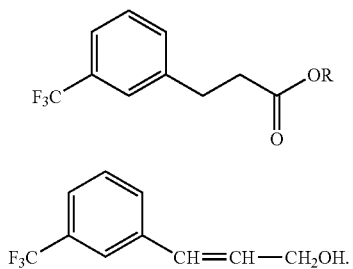

44. The process in claim 1, wherein the compound V is prepared from a mixture of compound II and compound IX of the following structure:

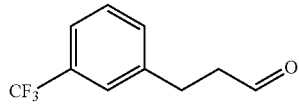

by reduction of the carbonyl wherein compound II is as follows:

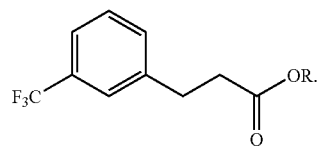

45. The process of claim 44, wherein the mixture of compounds II and IX is prepared from a mixture of compounds II and III by reduction of the carbonyl wherein compound III is as follows:

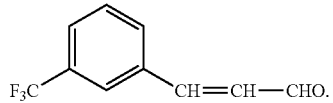

* * * * *

UNITED STATES PATENT AND TRADEMARK OFFICE
CERTIFICATE OF CORRECTION

PATENT NO.         : 7,250,533 B2                                        Page 1 of 2
APPLICATION NO. : 11/435430
DATED                 : July 31, 2007
INVENTOR(S)       : Lifshitz-Liron et al.

It is certified that error appears in the above-identified patent and that said Letters Patent is hereby corrected as shown below:

Column 5, scheme 6, change

" 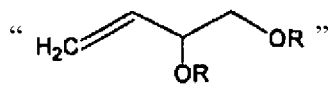 "

Acrolein dialkyl acetal to

-- 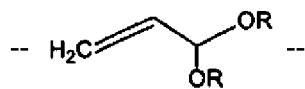 --

Acrolein dialkyl acetal

Column 5, scheme 6, change

" 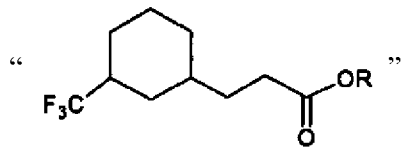 "

Compound II to

" 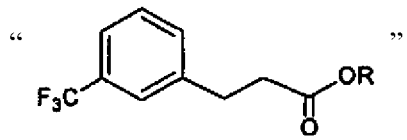 "

Compound II

Column 15, scheme 6, change

" 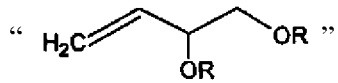 "

Acrolein dialkyl acetal

UNITED STATES PATENT AND TRADEMARK OFFICE
CERTIFICATE OF CORRECTION

PATENT NO. : 7,250,533 B2
APPLICATION NO. : 11/435430
DATED : July 31, 2007
INVENTOR(S) : Lifshitz-Liron et al.

It is certified that error appears in the above-identified patent and that said Letters Patent is hereby corrected as shown below:

to

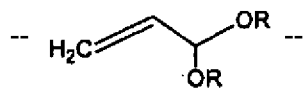

Acrolein dialkyl acetal

Column 15, scheme 6, change

" 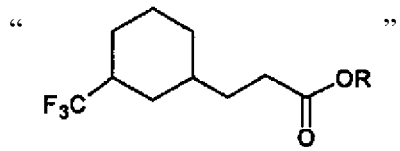 "

Compound II to

-- 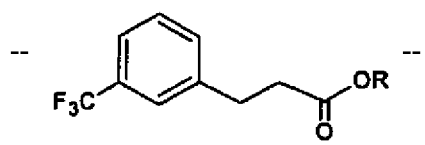 --

Compound II

Signed and Sealed this

Twenty-fifth Day of August, 2009

David J. Kappos
*Director of the United States Patent and Trademark Office*